(12) United States Patent
Merlin et al.

(10) Patent No.: US 6,340,571 B1
(45) Date of Patent: *Jan. 22, 2002

(54) **ANTIBODIES SPECIFIC FOR *STAPHYLOCOCCUS AUREUS*, AND USE THEREOF**

(75) Inventors: Sylviane Merlin, Caluire; Nicole Battail; Jean-Pierre Flandrois, both of Lyons; Gérard Carret, Feyzin, all of (FR)

(73) Assignee: Bio Merieux, Marcy l'Etoile (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/952,052

(22) PCT Filed: Mar. 21, 1997

(86) PCT No.: PCT/FR97/00510

§ 371 Date: Nov. 13, 1997

§ 102(e) Date: Nov. 13, 1997

(87) PCT Pub. No.: WO97/34931

PCT Pub. Date: Sep. 25, 1997

(30) Foreign Application Priority Data

Mar. 21, 1996 (FR) .............................. 96 03761

(51) Int. Cl.[7] ........................ G01N 33/569; C12N 5/06; C12N 5/16; C07K 16/00
(52) U.S. Cl. ...................... 435/7.33; 435/326; 435/332; 530/388.2; 530/388.4
(58) Field of Search .................. 530/387.1, 388.2, 530/388.4; 435/326, 332, 7.33

(56) References Cited

U.S. PATENT DOCUMENTS 5,242,824 A * 9/1993 Hellstrom et al.

FOREIGN PATENT DOCUMENTS

| EP | 137657 | * | 4/1985 |
| EP | A1 0-323331 | | 7/1989 |
| FR | A1 2-679923 | | 2/1993 |
| WO | WO-A 90-15077 | | 12/1990 |

OTHER PUBLICATIONS

Fournier et al (J. of Clinical Microbiology vol. 31, No. 5, May 1993 pp 1342–1344).*
Fattom et al (Infection & Immunity vol. 58 No. 7, Jul. 1990 pp 2367–2374).*
Galfre, G. et al. "Antibodies to Major Histocompatibility Antigens Produced by Hybrid Cell Lines." *Nature*, v 266, pp. 550–552, Apr. 1977.
Croize, J. et al. "Improved Identification of *Staphylococcus aureus* Using a New Agglutination Test. Results of an International Study," pp. 487–491, 1993.
Felten, Annie et al. "Analyse Critique des Tests de Dépistage Rapide de *Staphylococcus aureus*, Pastorex Staph Plus, Slidex Staph–Kit et *Staph aureus*, dans les Isolats Cliniques," Pathologie Biologie, vol. 43, No. 5, pp. 471–476, May 1995.

* cited by examiner

*Primary Examiner*—Mark Navarro
(74) *Attorney, Agent, or Firm*—Oliff & Berridge. PLC

(57) ABSTRACT

A monoclonal or polyclonal antibody specific for an epitope common to *Staphylococcus aureus* strains of various capsular serotypes, particularly methicillin-resistant strains, the antibody being selected from immunoglobulins G, M, and A, and the use thereof in a reagent for detecting *Staphylococcus aureus*.

10 Claims, No Drawings

ANTIBODIES SPECIFIC FOR *STAPHYLOCOCCUS AUREUS*, AND USE THEREOF

FIELD OF THE INVENTION

The present invention relates to the field of the detection of *Staphylococcus aureus* bacteria, and in particular strains of *Staphylococcus aureus* which are resistant to methicillin.

DESCRIPTION OF RELATED ART

"Detection" is understood to mean collectively all the techniques which make it possible to identify, qualitatively and/or quantitatively, or to enrich, purify or separate a biological analyte, in this case *Staphylococcus aureus* bacteria.

In accordance with the document EP-A-0 323 331, a reagent for detecting *Staphylococcus aureus* bacteria, including the methicillin-resistant strains, is known, this reagent comprising:

fibrinogen, an antibody recognized by *Staphylococcus aureus* protein A, an antibody specifically recognizing the type 5 capsular serotype of *Staphylococcus aureus* or an antibody specifically recognizing the type 8 serotype of *Staphylococcus aureus*, and preferably a mixture of these two antibodies.

SUMMARY OF THE INVENTION

According to the present invention, a monoclonal or polyclonal antibody is provided which specifically recognizes an epitope common to *Staphylococcus aureus* strains of various capsular serotypes, particularly the methicillin-resistant strains. This antibody is selected from the type G immunoglobulins, the type M immunoglobulins and the type A immunoglobulins.

A particularly advantageous application of the antibody according to the invention consists in incorporating it into a reagent specific for the detection of *Staphylococcus aureus*, including the methicillin-resistant strains. Compared with the document EP-A-0 323 331, the sensitivity of the reagent of the invention is superior, because the capacity for recognition of the capsular serotypes is greater.

Thus, according to the invention, there are provided and described:

a monoclonal or polyclonal antibody specific for an epitope common to the *Staphylococcus aureus* strains of various capsular serotypes, particularly the methicillin-resistant strains, the said antibody being selected from the type G immunoglobulins, the type M immunoglobulins and the type A immunoglobulins; this antibody specifically recognizes at the same time at least two different capsular serotypes of the said *Staphylococcus aureus* strains; preferably, it is selected from the type G immunoglobulins and the type M immunoglobulins;

a monoclonal or polyclonal antibody as defined above which in particular recognizes at least the type 5 capsular serotype and the type 8 capsular serotype of the said *Staphylococcus aureus* strains, a monoclonal antibody capable of being obtained according to a technique adapted from Galfre et al. (Nature, 266, 550–552, (1977)), using as initial cell line for the fusion, the myeloma line SP2/0-Ag14 (ATCC CRL 1581); the fusion is performed with spleen cells from mice of the BALB/C species and of the BALB/CBYJICO strain (marketed by the company IFFA Credo), immunized with a *Staphylococcus aureus* type 5 strain, according to conventional techniques; the clones obtained were screened by immunoenzymatic techniques (ELISA); the selected clones were reinjected by the intraperitoneal route into mice prepared beforehand for the production of ascitic fluid; each monoclonal antibody was used to sensitize latex particles and was tested for its specificity to recognize *Staphylococcus aureus* capsular polysaccharides; the monoclonal antibodies called P2G7A1E5 and P6D8D12E1 respectively were selected because of their specificity in recognizing an epitope common to various capsular serotypes, in particular of types 5 and 8;

a monoclonal antibody capable of being obtained, or as obtained from the hybridoma cell line deposited under the No. 96021514, on Feb. 15, 1996 with the ECACC;

a monoclonal antibody capable of being obtained, or as obtained from the hybridoma cell line deposited under the No. 96021513, on Feb. 15, 1996 with the ECACC;

a hybridoma cell line such as deposited under the No. 96021514, on Feb. 15, 1996 with the ECACC, or such as that deposited under the No. 96021513, on Feb. 15, 1996 with the ECACC, or any other derived hybridoma cell line, for example any progeny of this line; the cell lines are claimed as such, as well as any derived cell line, that is to say capable of producing antibodies exhibiting the same immunological characteristics as those described in the present invention;

a specific reagent for the detection of *Staphylococcus aureus* bacteria and particularly methicillin-resistant strains, comprising at least one antibody specifically recognizing at least one epitope common to the various capsular serotypes of the methicillin-resistant *Staphylococcus aureus* strains, the said reagent comprising at least one monoclonal or polyclonal antibody as defined above; the said antibody can be attached or coupled, or otherwise, to a support or a marker; monoclonal or polyclonal antibody is understood to mean the antibodies as defined above as well as any antibody exhibiting cross-specificity with the latter;

a specific reagent, particularly for the detection of *Staphylococcus aureus* bacteria and particularly of methicillin-resistant strains, comprising in addition fibrinogen or a compound based on fibrinogen, capable of being recognized by the *Staphylococcus aureus* affinity factor for fibrinogen; the fibrinogen or fibrinogen compound can be attached or coupled, or otherwise, to a support or to a marker;

a specific reagent, particularly for the detection of the bacteria *Staphylococcus aureus* and particularly for the methicillin-resistant strains, comprising in addition immunoglobulins or their Fc fragment recognized by *Staphylococcus aureus* protein A, attached or coupled, or otherwise, to a support or to a marker.

DESCRIPTION OF PREFERRED EMBODIMENTS

All sorts of support or marker can be envisaged according to the invention.

Particles in suspension can thus be used. These particles are in particular latex particles such as polystyrene beads or similar particles, preferably having a size of less than 2 µm. By way of example, there may be mentioned Estapor particles, marketed by the company RHONE-POULENC, such as:

polystyrene K080 particles having a diameter of 0.8 µm, polystyrene K109 particles having a diameter of 0.8 µm, polystyrene particles having carboxyl groups, PSI 480, having a diameter of 0.8 µm.

Magnetic gels, such as polyacrylamide and/or agarose gels containing magnetic particles can also be used. It is possible, in addition, to use gels such as Ultrogel and Magnogel (trademarks) from the company IBF.

The support used in a reagent according to the present invention may also be red blood cells, for example from sheep.

The support may be in the form of a plate, a cone, a strip, for example made of polystyrene or a styrene-based copolymer, a glass tube or the like.

The attachment of antibodies and of fibrinogen to particles in suspension, particularly of latex, may be achieved according to one of the following techniques:

by passive adsorption, it being possible for the attachment to be spontaneous, during incubation of the latex particles in a solution containing the antibodies and the fibrinogen; an incubation for example of about 2 hours at 20° C. is often sufficient;

by covalent bonding, it being possible for the attachment to be achieved by creating a covalent bond between the antibodies and the reactive groups present on some latex particles; it is possible for example to use a carbodiimide to create the covalent bond.

When the support consists of red blood cells, these may be sensitized beforehand with fibrinogen or any other appropriate molecule, according to conventional techniques.

The concentration of antibodies to be attached onto the latex particles, which should be determined for each antibody according to known methods, is usually between 0.1 µg and 100 µg of antibody proteins per millilitre of latex in solution.

In a reagent according to the invention, the antibodies and the fibrinogen may be attached onto a single suspension of particles, for example of latex, or alternatively may be attached onto suspensions of particles which are respectively different, such as red blood cells and latex particles, or various latexes which are then mixed in order to constitute the reagent.

The marker may be any biological or chemical molecule, for example an enzyme, a hapten, an oligonucleotide, a radioactive element and the like.

Other subjects of the invention are the following:

a reagent as defined above comprising an immunoglobulin-type antibody comprising an Fc fragment capable of attaching onto *Staphylococcus aureus* protein A and/or another compound based on fibrinogen or derivative, capable of reacting with the affinity factor for fibrinogen of the said bacteria, the said reagent further comprising at least one polyclonal or monoclonal antibody capable of specifically recognizing various capsular serotypes of *Staphylococcus aureus*, particularly types 5 and 8 serotypes;

a process for detecting in a biological sample *Staphylococcus aureus* bacteria, and particularly methicillin-resistant strains, characterized in that:

a reagent as defined above is made available, the said sample is brought into contact with the said reagent, the production of agglutination is observed.

The characteristics and advantages of the subjects of the invention are stated and illustrated below in Examples 1–3.

EXAMPLE 1

Composition of a Reagent According to the Invention, Called SLIDEX STAPH PLUS

The reagent comprises an immunoglobulin-type antibody comprising an Fc fragment capable of attaching onto *Staphylococcus aureus* protein A and/or another compound based on fibrinogen or derivative, capable of reacting with the affinity factor for fibrinogen of the said bacteria, the said reagent further comprising at least one polyclonal or monoclonal antibody capable of specifically recognizing various capsular serotypes of *Staphylococcus aureus*, particularly types 5 and 8 serotypes.

EXAMPLE 2

Process for the Production of the Antibody Contained in the Reagent of Example 1 a) Preparation of spleen cells from mice immunized with a *Staphylococcus aureus* strain Material:

*Staphylococcus aureus* strains CIP103313 of capsular serotype 5 and CIP108314 of capsular serotype 8.

Culture medium: Columbia agar+5% sheep blood.

Method:

The strains preserved at −80° C. are cultured twice on sheep blood agar.

The colonies are suspended in physiological saline at the concentration of $3 \times 10^9$ microorganisms/ml.

A method of inactivation was used: inactivation at 70° C. for 1 hour.

The vaccines are freshly prepared.

Origin of the cell culture:

*Staphylococcus aureus* strain of capsular serotype 5

Animal for immunization: female mice of the BALB/C species and of the BALB/CBYJICO strain (provided by IFFA Credo)

Myelomatous line SP2/0-AG14.

Immunization protocol:

| | | |
|---|---|---|
| J = 0 | $3 \times 10^8$ microorganisms + CFA (1:1) | IP |
| J = 7.14 | $3 \times 10^8$ microorganisms | IP |
| J = 28.76 | $3 \times 10^8$ microorganisms | IP |
| J = 204 | Booster $3 \times 10^8$ microorganisms in 9% NaCl | IV |
| J = 207 | Fusion of 29/01/93, mouse No. 1 series 010 | |

Culture in suspension

Ploidy: heteroploid

Culture conditions:

Basic medium: Iscove's Modified Dulbecco Medium supplemented with sodium bicarbonate (3024 mg/l), 10% foetal calf serum (FCS), PH 6.7 to 7.3, temperature 25° C.

Additional reagents: insulin (5 µg/l), 2-mercaptoethanol (10 µM), ethanolamine (20 µM), penicillin (100 U/ml), streptomycin (50 µg/ml).

Subculturing technique: the cells are subcultured every 2 or 3 days.

Freezing of the cells:

Composition of the medium: IMDM supplemented with 10% FCS and 10% DMSO (dimethyl sulphoxide—Sigma)

Cellular concentration: $3.6 \times 10^6$ cells per ampoule ($2 \times 10^6$ cells/ml)

Method: slow freezing of the cells at −80° C. in IMDM medium—10% FCS—10% DMSO, 24 h to 72 h, then storage in liquid nitrogen −180° C.

b) Identification of the stable hybridoma

Number of clonings carried out: 2

Name of the clone : 6D8D12El

Isotyping: IgG2b,K

Synthesis capacity: level of Ig's secreted into the supernatant: ND.

Antigenic specificity:

Indirect ELISA (1)

NUNC-maxisorb plates coated with 50 µl of STAPH 5 microorganisms ($10^9$ g/ml), dried overnight at 37° C., saturate with 100 µl of PBS-milk 1% for 1 h at 37° C., saturate with 100 µl of PBS-horse serum 1%, incubate for 1 h at 37° C., add 100 µl of supernatant or of ascitic fluid diluted in PBS-Tween 20 0.05%, and then incubated 1 h at 37° C., add 100 µl of Ig's anti-mouse Ig(H+L) conjugated to ALP (Jackson Laboratories batch 24724) diluted 1/2000 in PBS-BSA 1% +horse serum 1%, 1 h at 37° C., add 100 µl of PNPP (BioMérieux ref. 60002990) at the concentration of 2 mg/ml in DEA-HCL (Biomérieux ref. 60002989), pH 9.8, incubated 30 min at 37° C., block the reaction with 100 µl of 1 N NaOH.

NB: 3 washes are performed between each step with 300 µl of Pbs-tween 20 0.05% and an additional wash with distilled water before adding the PNPP.

RESULTS of (1): this antibody is specific for *S. aureus* and does not recognize either *S. Warneri, S. Hominis, S. Epidermidis, S. Cohnii* or *S. Haemolyticus*.

It recognizes the *S. aureus* type 5, type 8, type B, type A and type MC31, and the non-5 and non-8 strains (Ex: strains 1033, K8, 16N15).

Direct agglutination technique (2)

In round-bottomed plates (Biomérieux M220 24A ref. 96350), place 50 µl of supernatants diluted in PBS +50 µl of microorganisms at $5 \times 10^8$ g/ml; stir the plates and then incubate at 22° C. The reading is performed by eye, about 15 hours later.

RESULTS of (2): agglutination visible by eye (4+).

c) Production of antibodies in vivo

Animal used: female mice 4–6 weeks old, of the BALB/C species, of the BALB/CBYJICO strain (IFFA Credo).

Preparation of inoculum: the cellular suspension is centrifuged at 200 g, 10 minutes, 25° C. The cells are resuspended in 9% NaCl in an amount of $10^6$ cells/ml, Injection of $10^6$ cells/mouse by the intraperitoneal route, for 20 mice, Time of harvesting the ascitic fluid: 10 days+2 days, Volume of ascites: 245.5 ml, Volume of the pool: 230.5 ml, Yield: 93.9%,

EXAMPLE 3

Comparison of the Sensitivity and of the Specificity of the SLIDEX STAPH PLUS Reagent and of Those of Various Commercialized Reagents, in the Detection of Various *Staphylococcus aureus* Strains The SLIDEX STAPH PLUS reagent was compared with the following reagents:

SLIDEX STAPH KIT: ref. 7 311 2 batch 674145 B (exp. April 1996), marketed by the Applicant, STAPHYSLIDE: ref. 5 508 1 batch 674775 A (exp. September 1996), marketed by the Applicant, PASTOREX STAPH PLUS marketed by Diagnostic Pasteur: ref. 56356 batch 4LO42R (exp. February 1996) and batch SE 047 R (exp. July 1996), STAPHAUREX PLUS marketed by Murex: ref. ZL 33 batch K61691 0 (exp. Jan. 1, 1995) and batch K9251 1 0 (exp. August 1996).

To determine the sensitivity of each of these reagents, the following 346 *Staphylococcus aureus* strains were tested:

118 *S. aureus* strains resistant to methicillin and not having the affinity factor for fibrinogen (Clumping Factor negative) (origin: France, Germany, England, Benelux, Italy, Spain, USA, USA Kansas)

131 *S. aureus* strains resistant to methicillin and having the affinity factor for fibrinogen (Clumping Factor positive) (origin: France, Germany, England, Benelux, Italy, Spain, USA, Australia, Hong Kong)

97 methicillin-sensitive *S. aureus* strains (origin: France, England, Benelux, Italy, Spain, Poland, Australia, Hong Kong)

In addition, to determine the specificity of each of these reagents, 155 Staphylococcus non-aureus strains were tested (origin : France, Germany, England, Benelux, Italy, Spain, Poland, USA, Australia, Hong Kong).

The strains were cultured on Columbia agar+5% sheep blood.

a) Sensitivity results obtained with the 118 *S. aureus* strains resistant to methicillin and not having the affinity factor for fibrinogen The results are assembled in Table 1 below:

TABLE 1

| Number of strains | Slidex Staph Plus | Slidex Staph Kit | Pastorex Staph Plus | Staphaurex Plus |
|---|---|---|---|---|
| 76 | + | + | + | + |
| 1 | + | + | + | unint. |
| 1 | + | + | unint. | + |
| 1 | + | + | − | + |
| 9 | + | + | + | − |
| 4 | + | + | − | − |
| 18 | + | − | + | + |
| 1 | + | − | + | − |
| 5 | + | − | − | − |
| 1 | − | + | + | + |
| 1 | − | + | − | − |
| total: 118 | 116 | 94 | 106 | 97 |
| Sensitivity | 98.30% | 79.67% | 90.6% | 82.9% | unint. means "uninterpretable".

In accordance with Table 1, SLIDEX STAPH PLUS showed a significantly greater sensitivity (98.30%) than that of SLIDEX STAPH KIT (79.67%), PASTOREX STAPH PLUS (90.6%) and STAPHAUREX PLUS (82.9%).

b) Results obtained with the 131 *S. aureus* strains resistant to methicillin and having the affinity factor for fibrinogen The results are assembled in Table 2 below:

TABLE 2

| Number of strains | Slidex Staph Plus | Slidex Staph Kit | Pastorex Staph Plus | Staphaurex Plus |
|---|---|---|---|---|
| 123 | + | + | + | + |
| 2 | + | + | + | unint. |
| 4 | + | + | + | − |
| 2 | +* | + | +* | − |
| total: 131 | 131 | 131 | 131 | 123 |
| Sensitivity | 100% | 100% | 100% | 95.35% |

*slow agglutination
unint. means "uninterpretable".

c) Results obtained with the 97 methicillin-sensitive *S. aureus* strains

The results are assembled in Table 3 below:

TABLE 3

| Number of strains | Slidex Staph Plus | Slidex Staph Kit | Staphyslide | Pastorex Staph Plus | Staphaurex Plus |
|---|---|---|---|---|---|
| 94 | + | + | + | + | + |
| 1 | + | unint. | + | + | + |
| 2 | + | unint. | unint. | + | + |
| total: 97 | 97 | 94 | 95 | 97 | 97 |
| Sensitivity | 100% | 100% | 100% | 100% | 100% | unint. means "uninterpretable".

In accordance with this table, all the strains were detected, giving a sensitivity of 100% for each of the reagents.

d) Results obtained with the 155 S. non-aureus strains

The results are assembled in Table 4 below:

| Staphylococcus non-aureus (number) | Slidex Staph Plus | | | Slidex Staph Kit | | | Staphyslide | | |
|---|---|---|---|---|---|---|---|---|---|
| | + | − | UNINT | + | − | UNINT | + | − | UNINT |
| *S. epidermidis* (45) | 2 | 43 | 0 | 9 | 25 | 11 | 5 | 30 | 10 |
| *S. simulans* (8) | 0 | 8 | 0 | 3 | 5 | 0 | 0 | 8 | 0 |
| *S. hyicus* (3) | 1 | 2 | 0 | 0 | 3 | 0 | 0 | 3 | 0 |
| *S. saprophiticus* (10) | 0 | 9 | 1 | 0 | 9 | 1 | 0 | 9 | 1 |
| *S. haemolyticus* (20) | 0 | 20 | 0 | 8 | 12 | 0 | 0 | 20 | 0 |
| *S. warneri* (12) | 0 | 12 | 0 | 3 | 9 | 0 | 0 | 12 | 0 |
| *S. hominis* (14) | 0 | 13 | 1 | 7 | 5 | 2 | 2 | 11 | 1 |
| *S. lugdunensis* (5) | 0 | 5 | 0 | 0 | 5 | 0 | 0 | 5 | 0 |
| *S. schleiferi* (4) | 3 | 1 | 0 | 3 | 1 | 0 | 3 | 1 | 0 |
| *S. cohnii* (4) | 1 | 3 | 0 | 3 | 1 | 0 | 0 | 4 | 0 |
| *S. capitis* (3) | 0 | 3 | 0 | 0 | 3 | 0 | 0 | 3 | 0 |
| *S. sciuri* (10) | 3 | 7 | 0 | 0 | 8 | 2 | 0 | 8 | 2 |
| *S. lentus* (2) | 0 | 2 | 0 | 0 | 2 | 0 | 0 | 2 | 0 |
| *S. xylosus* (2) | 0 | 1 | 1 | 0 | 0 | 2 | 0 | 0 | 2 |
| *S. auricularis* (1) | 0 | 1 | 0 | 1 | 0 | 0 | 0 | 1 | 0 |
| *S. chromogenes* (4) | 0 | 4 | 0 | 0 | 4 | 0 | 0 | 4 | 0 |
| *S. caseolyticus* (1) | 0 | 1 | 0 | 0 | 1 | 0 | 0 | 1 | 0 |
| *S. intermedium* (7) | 1 | 2 | 4 | 2 | 4 | 1 | 2 | 5 | 0 |
| Total (155) | 11 | 137 | 7 | 39 | 97 | 19 | 12 | 127 | 16 |
| Specificity | | 137/148 92.57% | | | 97/136 71.32% | | | 127/139 91.37% | |

| Staphylococcus non-aureus (number) | Pastorex Staph Plus | | | Staphaurex Plus | | |
|---|---|---|---|---|---|---|
| | + | − | UNINT | + | − | UNINT |
| *S. epidermidis* (45) | 1 | 44 | 0 | 2 | 43 | 0 |
| *S. simulans* (8) | 0 | 8 | 0 | 2 | 6 | 0 |
| *S. hyicus* (3) | 0 | 3 | 0 | 1 | 2 | 0 |
| *S. saprophiticus* (10) | 0 | 9 | 1 | 1 | 8 | 1 |
| *S. haemolyticus* (20) | 1 | 19 | 0 | 0 | 20 | 0 |
| *S. warneri* (12) | 0 | 12 | 0 | 0 | 12 | 0 |
| *S. hominis* (14) | 3 | 10 | 1 | 0 | 13 | 1 |
| *S. lugdunensis* (5) | 2 | 3 | 0 | 2 | 3 | 0 |
| *S. schleiferi* (4) | 3 | 1 | 0 | 3 | 1 | 0 |
| *S. cohnii* (4) | 2 | 2 | 0 | 1 | 3 | 0 |
| *S. capitis* (3) | 0 | 3 | 0 | 0 | 3 | 0 |
| *S. sciuri* (10) | 2 | 6 | 2 | 2 | 5 | 3 |
| *S. lentus* (2) | 0 | 2 | 0 | 0 | 2 | 0 |
| *S. xylosus* (2) | 1 | 0 | 1 | 1 | 0 | 1 |
| *S. auricularis* (1) | 0 | 1 | 0 | 0 | 1 | 0 |
| *S. chromogenes* (4) | 0 | 4 | 0 | 1 | 3 | 0 |
| *S. caseolyticus* (1) | 0 | 1 | 0 | 0 | 1 | 0 |
| *S. intermedium* (7) | 2 | 2 | 3 | 1 | 4 | 2 |
| Total (155) | 17 | 130 | 8 | 17 | 130 | 8 |
| Specificity | | 130/147 88.44% | | | 130/147 88.44% | |

The *S. epidermidis, S. simulans, S. hyicus* species may have a capsule.

The *S. lugdunensis, S. schleiferi, S. hyicus, S. interrmedius* species may have the affinity factor for fibrinogen.

The specificities of PASTOREX STAPH PLUS and STAPHAUREX are identical (88.44%) but less than those of STAPHYSLIDE (91.37%) and of SLIDEX STAPH PLUS (92.57%).

e) Performances of the reagents

Table 5 below indicates the results of sensitivity and specificity of each of the reagents.

TABLE 5

| | SENSITIVITY | | | | | |
|---|---|---|---|---|---|---|
| | *S. aureus* meti R | | | | | |
| | Clumping Factor | | All the meti R | *S. aureus* | All the *S. aureus* | |
| REAGENTS | negative | positive | strains | meti S | strains | SPECIFICITY |
| Slidex staph Plus | 98.30% | 100% | 99.2% | 100% | 98.84% | 92.57% |
| Slidex staph kit | 79.67% | 100% | 90.36% | 100% | 93.0% | 71.32% |
| Staphyslide | 0 | 100% | 52.61% | 100% | 65.7% | 91.37% |
| Pastorex Staph Plus | 90.6% | 100% | 95.56% | 100% | 96.81% | 88.44% |
| Staphaureux Plus | 82.9% | 95.35% | 89.43% | 100% | 92.42% | 88.44% |

In this table, as in the following tables where they appear, the expressions meti R, meti S mean "methicillin-resistant" and "methicillin-sensitive" respectively.

It is evident from this table that the sensitivity of SLIDEX STAPH PLUS (99.2%) is significantly greater than the other reagents; this superiority is essentially due to a better performance on the *S. aureus* strains resistant to methicillin and not having the affinity factor for fibrinogen.

What is claimed is:

1. An isolated monoclonal antibody specific for an epitope of *Staphylococcuis acreus* strains of various capsular serotypes, wherein said antibody is selected from type G immunoglobulins, type M immunoglobulins and type A immunoglobulins, and wherein said antibody binds to at least a type 5 capsular scrotype and a type 8 capsular scrotype of said *Staphylococcus aureus* strains, and wherein said antibody is obtained from a hybridoma cell line deposited under No. 96021514 with the ECACC or a hybridoma cell line deposited under No. 96021513 with the ECACC.

2. The antibody according to claim 1, wherein said antibody that is obtained by fusion between a myeloma line SP2/0-Ag14 (ATCC CRL 1581) and spleen cells from mice of a BALB/C species and of BALB/CBYJICO strain, is immunized with a *Staphylococcus aureus* strain.

3. The antibody according to claim 1, where said antibody is obtained from a hybridoma cell line deposited under No. 96021514 with the ECACC.

4. The antibody according to claim 1, wherein said antibody is obtained from a hybridoma cell line deposited under No. 96021513 with the ECACC.

5. The antibody according to claim 1, wherein the antibody is attached or coupled to a support or a marker.

6. The antibody according to claim 5, wherein fibrinogen or a compound based on fibrinogen that binds to the *Staphylococcus aureus* affinity factor for fibrinogen is attached or coupled to the support or the marker.

7. The antibody according to claim 5, wherein one or more antibodies that binds to *Staphylococcus aureus* protein A is attached or coupled to the support or the marker.

8. A process for detecting, in a biological sample, *Staphylococcus aureus* bacteria strains comprising:
    selecting an antibody according to claim 1,
    contacting said sample with said antibody, and
    observing production of agglutination.

9. A hybridoma cell line, wherein the hybridoma cell line is a progeny of the cell line deposited under No. 96021514 with the ECACC or the cell line deposited under No. 96021513 with the ECACC.

10. A hybridoma cell line selected from the group consisting of the cell line deposited under No. 96021514 with the ECACC and the cell line deposited under No. 96021513 with the ECACC.

* * * * *